(12) United States Patent
Hivert

(10) Patent No.: US 11,406,794 B2
(45) Date of Patent: Aug. 9, 2022

(54) NEEDLE HUB AND IV CATHETER SYSTEM COMPRISING SUCH NEEDLE HUB

(71) Applicant: Vigmed AB, Helsingborg (SE)

(72) Inventor: Magnus Hivert, Kallarekroken (SE)

(73) Assignee: Greiner Bio-One GmbH, Kremsmunster (AT)

( * ) Notice: Subject to any disclaimer, the term of this patent is extended or adjusted under 35 U.S.C. 154(b) by 0 days.

(21) Appl. No.: 15/541,273

(22) PCT Filed: Dec. 30, 2015

(86) PCT No.: PCT/EP2015/081459
§ 371 (c)(1),
(2) Date: Jun. 30, 2017

(87) PCT Pub. No.: WO2016/107922
PCT Pub. Date: Jul. 7, 2016

(65) Prior Publication Data
US 2017/0361070 A1 Dec. 21, 2017

(30) Foreign Application Priority Data
Jan. 2, 2015 (SE) .................... 1550001-0

(51) Int. Cl.
*A61M 25/06* (2006.01)
*A61M 5/32* (2006.01)
*A61M 25/00* (2006.01)

(52) U.S. Cl.
CPC ........ *A61M 25/0606* (2013.01); *A61M 5/329* (2013.01); *A61M 25/0097* (2013.01); *A61M 25/0618* (2013.01); *A61M 25/0625* (2013.01); *A61M 25/0631* (2013.01); *A61M 2005/325* (2013.01)

(58) Field of Classification Search
CPC .......... A61M 25/0606; A61M 25/0618; A61M 5/329; A61M 2005/325; A61M 25/0612; A61M 25/0625; A61M 25/0631
See application file for complete search history.

(56) References Cited

U.S. PATENT DOCUMENTS 4,869,259 A * 9/1989 Elkins .................. A61B 8/0833
600/458
5,215,528 A * 6/1993 Purdy ................. A61M 5/3273
604/164.08
(Continued)

FOREIGN PATENT DOCUMENTS

CN 1589917 A 3/2005
CN 1863565 A 11/2006
(Continued)

OTHER PUBLICATIONS

Search Report dated Dec. 30, 2015; 2015/800720306.

*Primary Examiner* — Kevin C Sirmons
*Assistant Examiner* — Leah J Swanson
(74) *Attorney, Agent, or Firm* — Fishman Stewart PLLC

(57) ABSTRACT

An intravenous (IV) catheter system may include a catheter hub, a needle hub and a needle shield. The needle hub may include a needle having a high friction surface part. Furthermore, embodiments may include an open and closed IV catheter system. Embodiments may include a needle hub and a shielded needle system.

19 Claims, 5 Drawing Sheets

(56) References Cited

U.S. PATENT DOCUMENTS

| | | | | |
|---|---|---|---|---|
| 5,257,980 | A | * | 11/1993 | Van Antwerp .... A61M 25/0606 604/506 |
| 5,558,651 | A | * | 9/1996 | Crawford .......... A61M 25/0618 604/110 |
| 6,394,979 | B1 | * | 5/2002 | Sharp ...................... A61M 5/32 604/117 |
| 7,988,664 | B2 | * | 8/2011 | Fiser ................. A61M 25/0618 604/110 |
| 9,522,255 | B2 | * | 12/2016 | Knutsson .......... A61M 25/0618 |
| 2005/0075609 | A1 | | 4/2005 | Latona |
| 2011/0011149 | A1 | * | 1/2011 | McKinnon ............... B21G 1/08 72/367.1 |
| 2013/0030371 | A1 | * | 1/2013 | Knutsson .......... A61M 25/0618 604/164.08 |
| 2013/0090607 | A1 | * | 4/2013 | McKinnon ........ A61M 25/0097 604/247 |

FOREIGN PATENT DOCUMENTS

| | | | | |
|---|---|---|---|---|
| CN | 102958553 | A | | 3/2013 |
| CN | 203090190 | U | | 7/2013 |
| EP | 1003588 | B1 | | 5/2000 |
| WO | WO-9908742 | A1 | | 2/1999 |
| WO | WO-2013187827 | A1 | * | 12/2013 ........ A61M 25/0618 |
| WO | WO-2014107133 | A1 | | 7/2014 |

\* cited by examiner

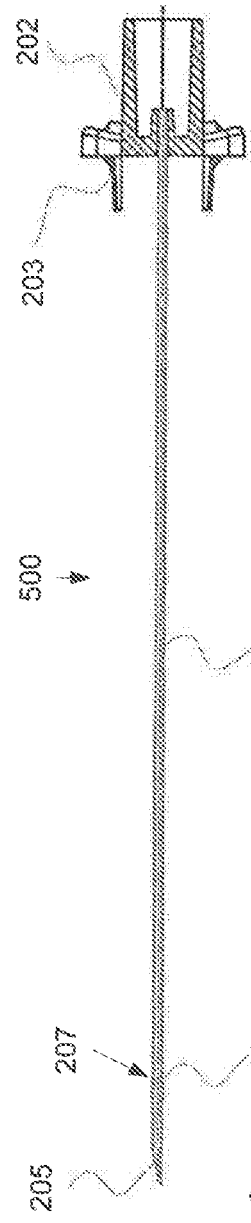
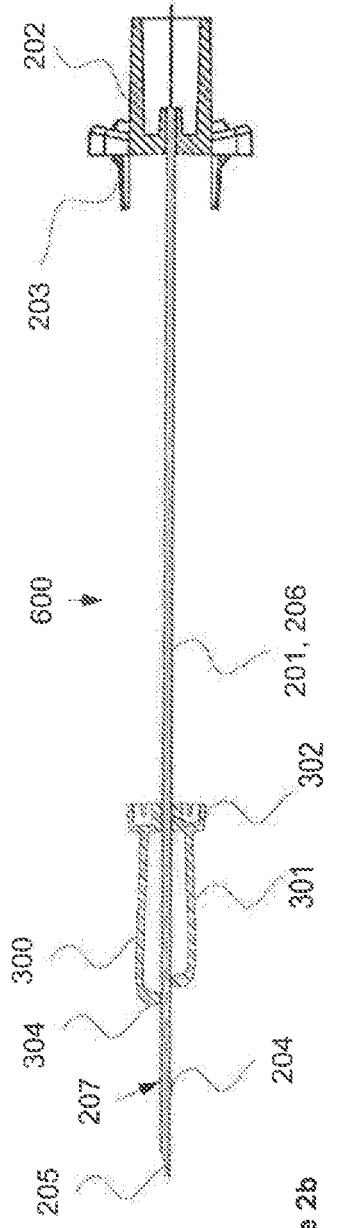
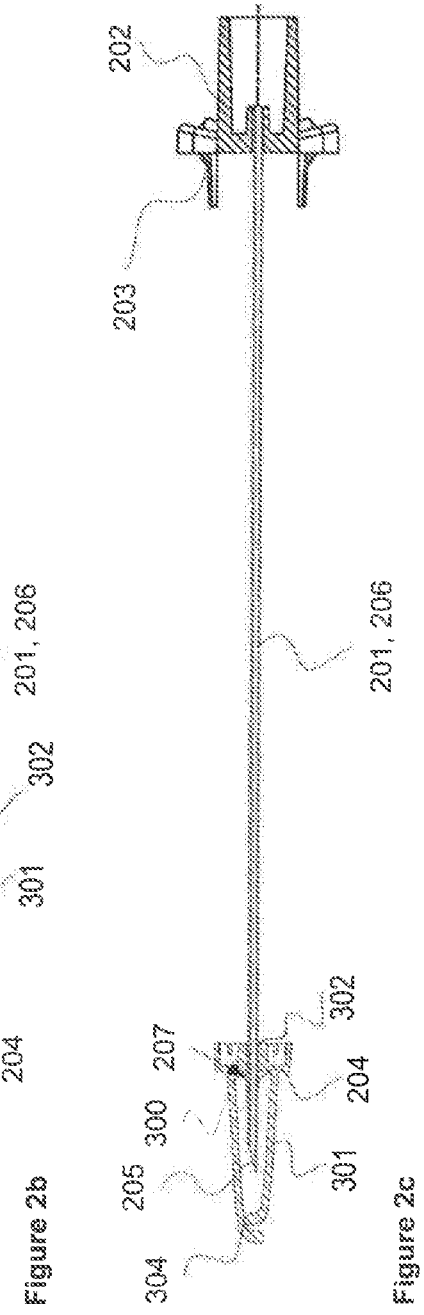
Figure 2a
Figure 2b
Figure 2c

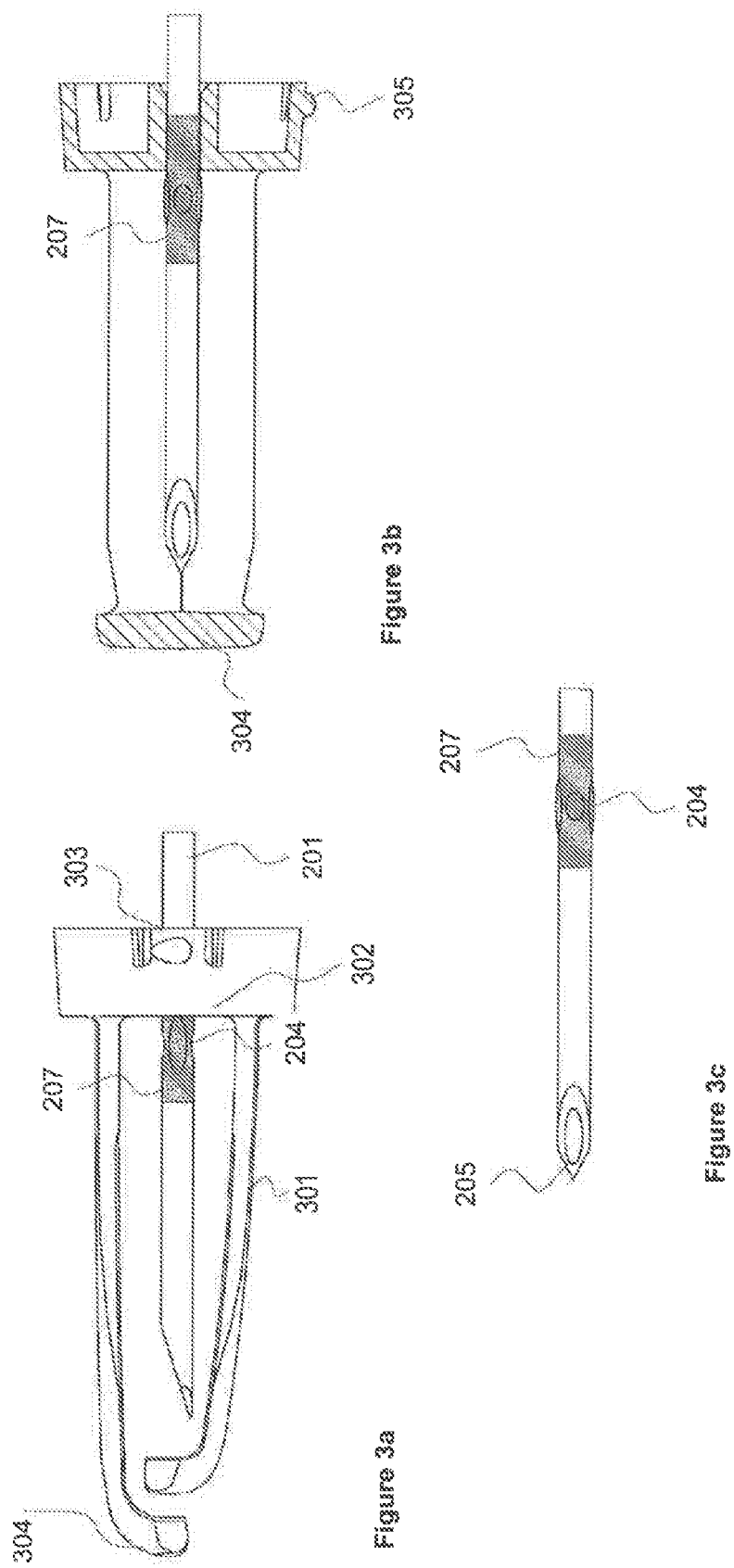

NEEDLE HUB AND IV CATHETER SYSTEM COMPRISING SUCH NEEDLE HUB

CROSS-REFERENCE TO RELATED APPLICATIONS

This application is a U.S. National phase based on, and claiming priority to, PCT/EP2015/081459, filed on Dec. 30, 2015 entitled "NEEDLE HUB AND IV CATHETER SYSTEM COMPRISING SUCH NEEDLE HUB," which is based on and claims priority to Swedish Patent Application No. 1550001-0, filed on Jan. 2, 2015, each of which is hereby incorporated by reference in its entirety.

FIELD OF THE INVENTION

The present invention pertains to an IV catheter system, comprising a needle hub, a catheter hub with a catheter connected distally of a catheter hub body, said catheter hub body having a catheter extending laterally from the catheter hub body, wherein the catheter is in fluid communication with an inner catheter hub body cavity and the lumen of the catheter, and a needle shield assembly. The invention also pertains to a needle hub for cooperation with such catheter hub into an IV catheter system.

BACKGROUND OF THE INVENTION

Catheters, particularly intravascular (IV) catheters, are used for infusing fluid, such as normal saline solution, various medicaments and total parenteral nutrition, into a patient, withdrawing blood from a patient or monitoring various parameters of the patient's vascular system. Peripheral IV catheters tend to be relatively short, and typically are on the order of about two inches or less in length. The most common type of IV catheter is an over-the-needle peripheral IV catheter.

As its name implies, an over-the-needle catheter is mounted over an introducer needle having a sharp distal tip. At least the distal portion of the catheter tightly engages the outer surface of the needle to prevent peelback of the catheter and thus facilitates insertion of the catheter into the blood vessel. The catheter and the introducer needle are assembled so that the distal tip of the introducer needle extends beyond the distal tip of the catheter with the bevel of the needle facing up away from the patient's skin.

The catheter and introducer needle assembly is inserted at a shallow angle through the patient's skin into a blood vessel. There are many techniques for inserting such a catheter and introducer needle assembly into a patient. In one insertion technique, the introducer needle and catheter are inserted completely into the blood vessel together. In another technique, the introducer needle is partially withdrawn into the catheter after the initial insertion into the blood vessel. The catheter is then threaded over the needle and inserted completely into the blood vessel.

The clinical utilization of a pointed hollow needle mounted inside a flexible catheter tube is well known in the medical art for the introduction of a catheter. In such a medical instrument, the catheter tube is positioned tightly around the needle in such a way as to allow the needle to slide and telescope along the length of the catheter tube. Before use, the tip of the needle is protruding slightly through the opening of the catheter tube to allow facile penetration through the skin. Upon puncturing of the skin and introduction of the needle, the distal end of the catheter tube is simultaneously brought into place inside the desired target body cavity of the patient, such as the inside of a blood vessel, for example a vein. The needle has then done its duty in assisting the introduction of the catheter and is withdrawn by being pulled backwards through the catheter. Upon release of the needle, the catheter is set in its intended working mode extending over a lengthier period of time and including, for example, periodical administration or infusion of fluids or medications in liquid form, the collection of blood samples and the like.

With regard to over-the-needle catheters, there are mainly two major alternatives. The first one, the open IV catheter system, comprises luer through which the needle is withdrawn after insertion of the catheter into the blood vessel, which is connectable to blood withdrawal or infusion means, as well as an optional port for the same purpose. The second one, the closed IV catheter system, comprises a septum in an catheter hub through which the needle is withdrawn after insertion of the catheter into the blood vessel, closing off the "needle channel" from the environment, and instead has an extension tube extending laterally from the catheter hub, wherein the extension tube is in fluid communication with the catheter hub cavity and the lumen of the catheter positioned in the blood vessel. These two alternatives are accompanied with different problems and benefits.

In recent years, there has been great concern over the contamination of clinicians with a patient's blood and a recognition that "blood contaminated sharps" must be disposed to avoid an accidental needle stick. This concern has arisen because of the advent of currently incurable and fatal diseases, such as Acquired Immunosuppressive Deficiency Syndrome ("AIDS"), hepatitis, etc., which can be transmitted by the exchange of body fluids from an infected person to another person.

As a result of the problem of accidental needlesticks by "blood contaminated sharps", various needle shields have been developed for use in conjunction with intravenous catheters.

In the field of medicine, such as within the field of devices for infusion and injection, it is known to arrange needle tip shielding devices on the injection or infusion needle, said shielding device having the ability to snap in front of the needle tip upon withdrawal of the needle. These needle tip shielding devices have historically been manufactured in stainless steel. After the manufacturing and packing of the devices for infusion and injection, the devices are sterilized for hygienic reasons.

Such a needle tip shielding device is for example disclosed in EP1003588. However, needle tip shielding devices will, when being arranged in for example a catheter hub, scratch and tear the polymeric catheter hub lumen, resulting in a major risk of flushing plastic material into the blood stream of the patient. Additionally, the manufacturing of such shielding devices of stainless steel is cumbersome and costly, since several punching and bending stations have to be used. Additionally, due to the metal sheet of such device, there is a high risk of "drawer effect" on the needle shaft.

A softer needle shielding device could be used to avoid such scratching. For instance, a plastic needle shield would not scratch the plastic of the catheter hub. However, the softer material characteristics of such a needle shield could also create the risk of it being able to slide over the stopper close to the needle tip, and off the needle.

Hence, a soft needle shield assembly with decreased risk of undue needle shield assembly release with regard to a IV catheter system, is desired.

SUMMARY OF THE INVENTION

Accordingly, the present invention preferably seeks to mitigate, alleviate or eliminate one or more of the aboveidentified deficiencies in the art and disadvantages singly or in any combination and solves at least the above mentioned problems by providing: an IV catheter system comprising a catheter hub, said catheter hub comprising: a tubular catheter, having a lumen, attached to a catheter hub body at its proximal end, with a catheter hub cavity in fluid communication with the lumen of the tubular catheter; a needle hub, said needle hub comprising: a needle extending distally from a needle hub body, said needle having a bulge and a high friction surface at its distal end zone; a needle shield comprising at least one resilient arm extending distally from a base plate, said base plate having a through hole for receiving the needle there through; wherein the needle hub is arranged in the catheter hub, such that the needle is slidingly arranged through the lumen of said catheter, such that the needle may be withdrawn proximally from the catheter hub; wherein the needle shield is arranged in the catheter hub cavity in a retained manner through cooperation between the needle shield and an inner wall of the catheter hub in said catheter hub cavity, and onto the needle, such that the at least one arm rests upon and is spring loaded by the needle, and the needle is slidingly arranged within the through hole of the base plate, in an assembled state; and wherein the outer diameter of the needle bulge is larger than the inner diameter of the through hole of the base plate when the needle hub is withdrawn from the catheter hub to release the needle shield from the catheter hub and the at least one arm will cover the tip of the needle in a released state: and such needle hub.

Advantageous features of the invention are defined in the dependent claims.

BRIEF DESCRIPTION OF THE DRAWINGS

These and other aspects, features and advantages of which the invention is capable will be apparent and elucidated from the following description of non-limiting embodiments of the present invention, reference being made to the accompanying drawings, in which FIG. 2a is a cross-sectional view of a needle system, according to one embodiment of the present invention;

FIG. 2b is a cross-sectional view of a shielded needle system, according to one embodiment of the present invention;

FIG. 2c is a cross-sectional view of a shielded needle system, according to one embodiment of the present invention;

FIG. 3a is a side view of a needle with a needle shield arranged thereon, covering the tip of the needle, according to one embodiment of the present invention;

FIG. 3b is a cross-sectional view of a needle with a needle shield arranged thereon, covering the tip of the needle, according to one embodiment of the present invention;

FIG. 3c is a top view of a needle, according to one embodiment of the present invention;

DETAILED DESCRIPTION OF THE EMBODIMENTS

Embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art.

Furthermore, the terminology used in the detailed description of the particular embodiments illustrated in the accompanying drawings is not intended to be limiting of the invention. More specifically, the term "proximal" refers to a location or direction of items or parts of items, during normal use of the IV catheter system disclosed herein, is closest to the user, i.e. the clinician, and farthest away from the patient receiving the IV catheter system. Similarly, the term "distal" refers to a location or direction of items or parts of items, during normal use of the IV catheter system disclosed herein, is closest to the patient and farthest away from the clinician. The term "laterally" refers to the direction away from the central axis of the IV catheter system, such that at least a vector component perpendicular to the central axis of the IV catheter system, wherein the needle and catheter of the assembled IV catheter system coincides with the central axis of the IV catheter system.

Figure 1A:
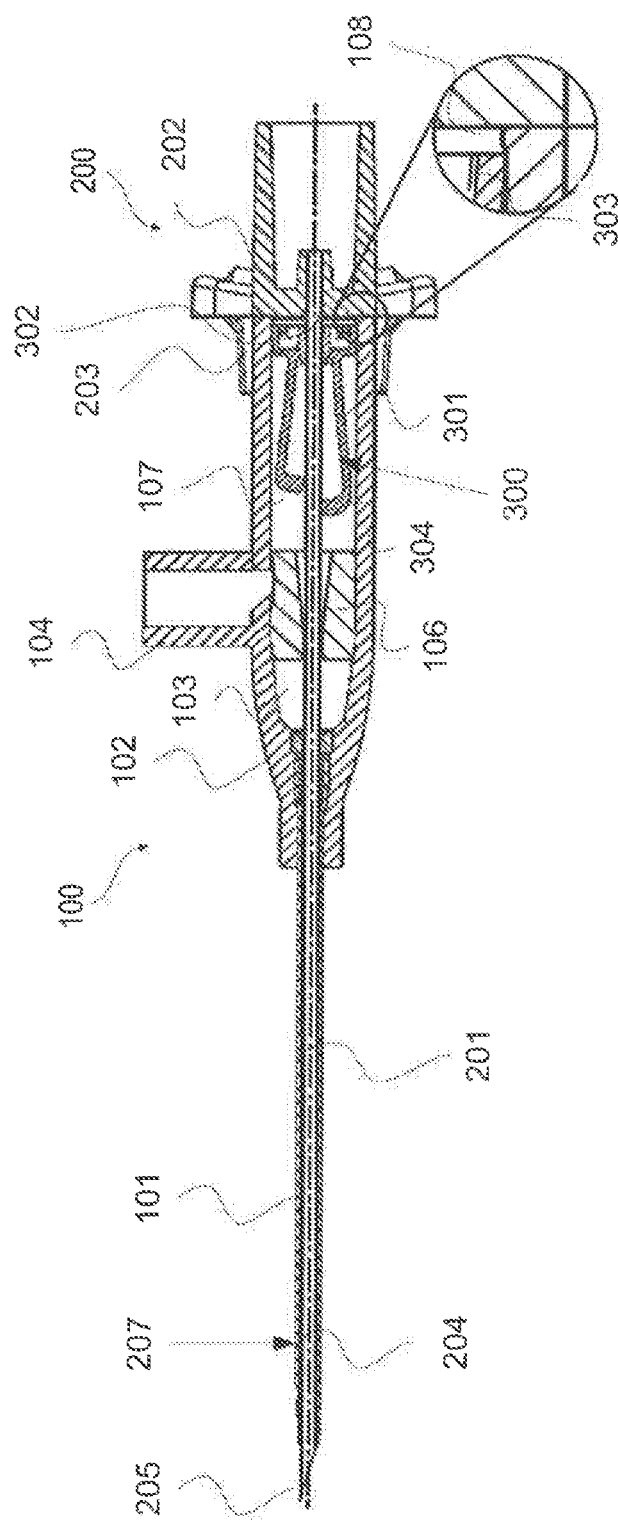
FIG. 1a is a cross-sectional view of an open IV catheter system, with a catheter hub, a needle hub, and a needle shield, in assembled state, in accordance with an embodiment of the present invention.

In accordance with FIG. 1a, one embodiment of a catheter hub 100 of an open IV catheter system is illustrated. The catheter hub 100 comprises a longitudinal and tubular catheter 101 at its distal end. The catheter 101 is, in accordance with above, intended to be inserted into a blood vessel of a patient. The catheter 101 is attached to a catheter hub body 102 at its proximal end, such that the catheter extends distally from the catheter hub body 102. The lumen of the catheter 101 is in fluid communication with a distal catheter hub cavity 103. The catheter hub body 102 is preferably made through injection molding, and then of a rigid plastic material suitable for injection molding and connection and interaction with other parts of the system. Such a suitable material is polycarbonate or a copolymer of polycarbonate and polyester.

In one embodiment in accordance with FIG. 1a, an open connector 104 is provided on a catheter hub body 102. The open connector 104 extends laterally from the catheter hub body 102. The open connector 104 may for example be tubular. The open connector 104 may be a luer fitting, such as a luer lock or luer slip, adapted to receive a syringe or tubing set in a known manner. The open connector 104 may have a lid, such as an injection port cap. The lid may be spring force operated. The open connector 104 connects to a bifunctional valve 106 in the distal catheter hub cavity 103, such that a tube or syringe may be connected to the tube connector 104 allowing for infusion through the open tube connector 104 into a proximal catheter hub cavity 107, further to the catheter 101 and finally into the blood stream of the patient, when there is no needle through the bifunctional valve 106 and catheter 101. The distal catheter hub cavity 103 ends proximally in a bifunctional valve 106. This bifunctional valve 106 has a central through-channel, which may be penetrated by a needle 201 of a needle hub 200, in accordance with FIG. 1a. When the needle 201 has been withdrawn from the catheter hub 100, the bifunctional valve 106 will keep said through channel open, such that the distal catheter hub cavity 103 is in contact with the proximal catheter hub cavity 107. Furthermore, the bifunctional valve 106 is preferably of a suitable rubber material or silicone. On the proximal side of the bifunctional valve 106 a proximal catheter hub cavity 107 is located. The proximal catheter hub cavity 107 is formed by the tubular wall of the catheter hub body 102 and a distal end wall in form of the proximal end wall of the bifunctional valve 106. This proximal catheter hub cavity 107, extending distally into the catheter hub body 102, is adapted in size and shape to house the needle shield 300, as disclosed in FIG. 1a.

The needle hub 200 comprises a needle 201 extending distally from a needle hub body 202 with a needle shaft 206, a needle tip 205, a bulge 204 and a high friction surface part 207 at its distal end zone, as seen in FIGS. 2a to 2c. The high friction surface part 207 may at least partly be applied on the bulge 204 and/or proximally of the bulge 204, i.e. closer to the needle hub body 202 than the bulge 204. The high friction surface part 207 may also cover the bulge 204, and extend proximally and/or distally of the bulge 204, To facilitate skin penetration, the high friction surface part 207 does however not cover the needle tip 205 and/or the part of the needle 201 extending distally beyond a catheter on an IV catheter system in a ready-to-use state.

The needle bulge 204 is a short section of the needle, where the radius of the bulge 204 is larger than that of the needle shaft 206. This may be achieved by a slight local deformation of the needle shaft 206. By a slight flattening of two opposing sides of the needle shaft 206, perpendicular to the length axis of the needle shaft 206, increased radius transitions between the flattened areas will protrude distally from the needle shaft and provide the bumps of the needle bulge 204, as seen in FIGS. 2a to 2c. The needle bulge 204 may also be obtained by for example providing the needle shaft 206 with a weld.

The needle bulge 204 area has a high friction surface part 207, covering at least the needle bulge 204, and may extend proximally and/or distally of the bulge 204 along the needle shaft 206.

In one embodiment in accordance with FIG. 2a, a needle system 500 is provided comprising a needle hub 200, wherein the needle hub 200 comprises a needle 201 extending distally from a needle hub body 202 with the needle bulge 204 at its distal end zone having a high friction surface part 207.

The needle shield 300 comprises a base plate 301. The base plate 301 is provided with a hole 302, extending there through, i.e. from the proximal side of the base plate 301 to the distal side of the base plate 301. Preferably, the hole 302 is arranged centrally on the base plate 301, such that arrangement of needle 201 through said hole 302 is facilitated while the needle 201 is arranged in accordance with the ready position of the catheter instrument. At least one resilient arm 304 is extending distally from an attachment point at said base plate 301. Preferably, due to manufacturing reasons, the attachment point is located at the periphery of the base plate 301. The resilient arm 304 has a resting state, from which it may be urged to yield free passage for the needle 201 through said hole 302 in an axial direction of said base plate 301 in a tension state. This released resting state is disclosed in FIG. 2c. The resilient arm 304 is in its tension state when the catheter instrument 100 is in its ready position, in accordance with FIG. 1a. The resilient arm 304 is adapted for clamping a needle tip 205 of a needle 201 extending through the hole 302 when the resilient arm 303 is in said resting state. For this reason, a straight imaginary line extending longitudinally through said hole 302 in the axial direction of said base plate 301 coincides with said at least one resilient arm 304 when said resilient arm 304 is in said resting state.

The needle shield 300 may comprise one, two, three or more tongues 303, which extend proximally from the lateral circular periphery of the base plate 301. The tongues 303 are, in accordance with above, resilient, whereby they are resiliently striving from a compressed state towards an expanded state. In the assembled state within the proximal catheter hub cavity 107, the tongues 303 are somewhat compressed, to exercise a force on the inner walls of the catheter hub 100. The needle shield 300 is thereby held therein, i.e. a constant spatial relationship between the needle shield 300 and the catheter hub 100 is provided. A plurality of tongues 303 may be evenly spread at the periphery of the base plate 301, whereby each tongue 303 is contacting the inner surface of the catheter hub 100 with essentially the same force.

The tongues 303 may comprise a protuberance 305 extending in a direction essentially perpendicular to the central axis or laterally of the needle shield 300. When the tongues 303 are provided with protuberances 305, the diameter of the base plate 301 in a transversal plane intersecting the protuberances 305 may be greater than the diameter of the proximal catheter hub cavity 107, and specifically the proximal opening thereof, along a transversal plane. Then the needle shield 300 may be compressed, due to the flexibility of the tongues 303, such that it may be inserted into the proximal catheter hub cavity 107 in a compressed state. In the inserted position, the protuberances 305 on the tongues 303 then exerts a retaining radially outwards directed pressure on the inner wall of the proximal catheter hub cavity 107. The ridge 108 of at the opening of the proximal catheter hub cavity 107 then maintains the needle shield 300 within the cavity, until the needle 201 bulge 204 pulls the stopping element proximally to the needle shield, whereby the pressure of the protuberances 305 on the inner walls of the proximal catheter hub cavity 107 is overcome and the also the protuberances 305 are pressed inwardly beyond the ridge 108 to safely release the needle shield 300 from the proximal catheter hub cavity 107. To facilitate interaction between the needle shield 300 and the proximal catheter hub cavity 107, the ridge 108 is somewhat slanting distally and/or proximally. The protuberances 305 are in the same way slanting distally and/or proximally. Preferably the slanting of the protuberances is sharper in the proximal direction than in the distal direction, whereby the needle shield 300 may be smoothly inserted into the proximal catheter hub cavity 107, retained with a snap action when the proximal side of the protuberances pass distally beyond the ridge 108, and also maintained more securely due to the sharper slanting at the proximal zone.

In one embodiment in accordance with FIG. 2b, a shielded needle system 600 is provided comprising a needle hub 200 and a needle shield 300. The needle hub 200 comprises a needle 201 extending distally from a needle hub body 202 with the needle bulge 204 at its distal end zone having a high friction surface part 207. The needle shield 300 is mounted on the needle, the needle shaft 206 extending through the hole of the needle shield base plate, the base plate being at the proximal end and the at least on resilient arm 304 at the distal end. The needle shield is mounted on the needle and located between the needle hub 200 and needle bulge 204.

The high friction surface part 207 is intended to cover at least the needle bulge 204, preferably extending proximally and possibly distally of the bulge 204, along the needle shaft 206. The length of the high friction surface part 207, from its distal end to its proximal end, may vary due to factors such as the diameter of the needle, but is in the range of 0.2 to 20 mm, preferably 0.5 to 5 mm. The friction coefficient between the normally polished steel alloy of the needle and a fatter plastic can be lower than 0.05 (μs). This is a positive property for optimal operation of the needle shield, ensuring smooth and quiet needle movement through the through hole of the needle shield base plate 301. However, the modulus of elasticity of a polymer body such as the needle shield 300, is low (polymer (PC) 2300 MPa or (LCP) 7000 MPa), resulting in that with a polished (low friction) needle bulge, there is a risk of the needle shield 300 deforming enough to be forced past the needle bulge 204. By providing a high friction surface part 207 on the needle bulge 204, the friction coefficient is increased up to 20-fold between the needle shield 300 and the high friction surface part 207 of the needle bulge 204. This greatly increases the force required for the needle shield 300 to be forced past the needle bulge 204. The surface roughness of a polished needle for medical purposes is 0.2 $R_a$. Hence, the surface roughness of the high friction surface part 207 is selected to be above 0.2 $R_a$, such as 0.25 to 25 $R_a$, and more preferably 0.25 to 10 $R_a$, and even more preferably from 0.5 to 5 $R_a$, such as 0.75 to 3 Ra. In this way, the surface roughness is adapted not to interact with the catheter, upon withdrawal of the needle hub 200 from the catheter hub 100, while simultaneously allowing for increased interaction between the needle shield 300 and the needle 201 of the needle hub 200, and more precisely the bulge 204 and the needle shield 300, such that needle shield 300 will be better retained on the needle 201.

By extending the high friction surface part 207 along the needle shaft 206, proximally of the needle bulge 204, the needle shield 300 will be subjected to high friction contact with the needle shaft 206 already before the needle shield base plate 301 interacts with the needle bulge 204. This is even more pronounced if the needle shield 300 experiences any lateral force or is tilting slightly in relation to the length axis of the needle shaft 206. This will result in increased drag between the needle shield 300 and the needle shaft 206 just before the needle shield base plate 301 makes contact with the needle bulge 204, providing part of the force required to release the needle shield 300 from the catheter hub 100, making it easier for the needle bulge 204 to release the needle shield 300.

The high friction surface part 207 can be achieved by processes, such as sandblasting, etching (chemical process), erosion, electron beam surface treatment, plasma treatment, electrical discharge machining and laser texturing. Optionally, the high friction surface part 207 could be achieved by adding a surface layer or surface film, such as a high-friction coating or layer, on the area of the high friction surface part 207.

The needle shield 300 is intended to be arranged on the needle 201 of the needle hub 200, which in turn is intended to be arranged in the catheter hub 100. In such assembled state, in accordance with FIG. 1a, the needle 201 penetrates the bifunctional valve 106, and extends through the catheter 101. Preferably, the needle 201 extends just beyond the distal end of the catheter 101, such that skin and blood vessel penetration is facilitated. In that position, the needle shield 300 is arranged in the proximal catheter hub cavity 107, with arms 304 thereof forced laterally by needle 201. The needle shield 300 preferably does not extend proximally of the proximal end of the catheter hub 100, but is instead entirely housed in the proximal catheter hub cavity 107 of the catheter hub 100. In this way, the needle hub body 202 of the needle hub 200 may cooperate with the catheter hub body 102 of the catheter hub 100, without intermediary structures, such as the needle shield 300. This may be accomplished through a distal connective flange 203 on the needle hub 200. The distal connective flange 203 may then house the distal end of the catheter body 102 of the catheter hub 100. This connection may be a snap fit. Alternatively, the needle hub body 202 has a distal cavity for housing a part of the needle shield 300, while still being adapted to be connectable to the catheter hub body 102. In this position the needle shield 300 is held in place in the proximal catheter hub cavity 107 through interaction between a needle shield base plate 301 and the inner tubular wall of the catheter hub body 102. This may be accomplished by tongues 303, extending laterally of the base plate 301, being flexed somewhat inwardly to exercise a lateral pressure on the inner tubular wall of the catheter hub body 102 inside the proximal catheter hub cavity 107. To further increase the cooperation between the periphery of the needle shield 300 and the catheter hub 100 a circumferential ridge 108 may be formed at the opening of the proximal catheter hub cavity 107. The base plate 301 is provided with a centrally arranged through hole, such that the needle 200 may run freely therein.

When withdrawing the needle hub 200 from the catheter hub 100, after the catheter 101 has been securely placed inside the blood vessel of the patient, the needle hub 200 will firstly be disconnected from the cooperation between the catheter hub body 102 and the needle hub body 202, such as through release of the connective flange 203 from the circumference of the catheter body 102. Then the needle 201 travels proximally within the catheter 101, until the needle tip 205 of the needle 201 exits the catheter 101 and enters the catheter hub body 102. When entering the catheter hub body 102, the needle tip 205 of the needle 201 will continue proximally into the distal catheter hub cavity 103 and further through the bifunctional valve 106. When the needle tip 205 of the needle 201 exits the bifunctional valve 106 on the proximal side thereof, the needle tip 205 of the needle 201 enters the proximal catheter hub cavity 107 of the catheter hub 100, wherein the needle shield 300 is securingly interacting with the inner tubular wall of the catheter hub body 102. When the needle tip 205 of the needle 201 passes proximally of the arms 304, the arms 304 will snap centrally to cover the needle tip 205 of the needle 200. This may be further facilitated by hooked tips on the arms 304. Just subsequently to the snapping of the arms 304 in front of the tip of the needle 201, a the high friction surface part 207 surrounding the bulge 204 on the needle 201 contacts the distal side of the needle shield 300 base plate 301. Thus, the withdrawal of the needle hub 200 further proximally will safely pull out the needle shield 300 from the proximal catheter hub cavity 107. This is accomplished by adapting the retaining action from tongues 303, such that the retaining force from these is overcome by a suitable withdrawal force. The high friction surface part 207 of the needle bulge 204 will ensure that the suitable withdrawing force is applied to the needle shield 300, to ensure safe release the needle shield from the proximal catheter hub cavity 107. Then the needle hub is separated from the catheter hub, and the needle shield 300 is securely arranged on the tip of the needle 200 to prohibit and prevent accidental needle stick, as can be seen in FIGS. 2c, 3a and 3b. When the needle tip 205 of the needle 201 has exited the proximal side of the bifunctional valve 106, the bifunctional valve 106 will provide an open connection between the distal catheter hub cavity 103 and the proximal catheter hub cavity 107. At the same time, the bifunctional valve 106 will open up the connection between the open connector 104 and the proximal catheter hub cavity 107.

Figure 4:
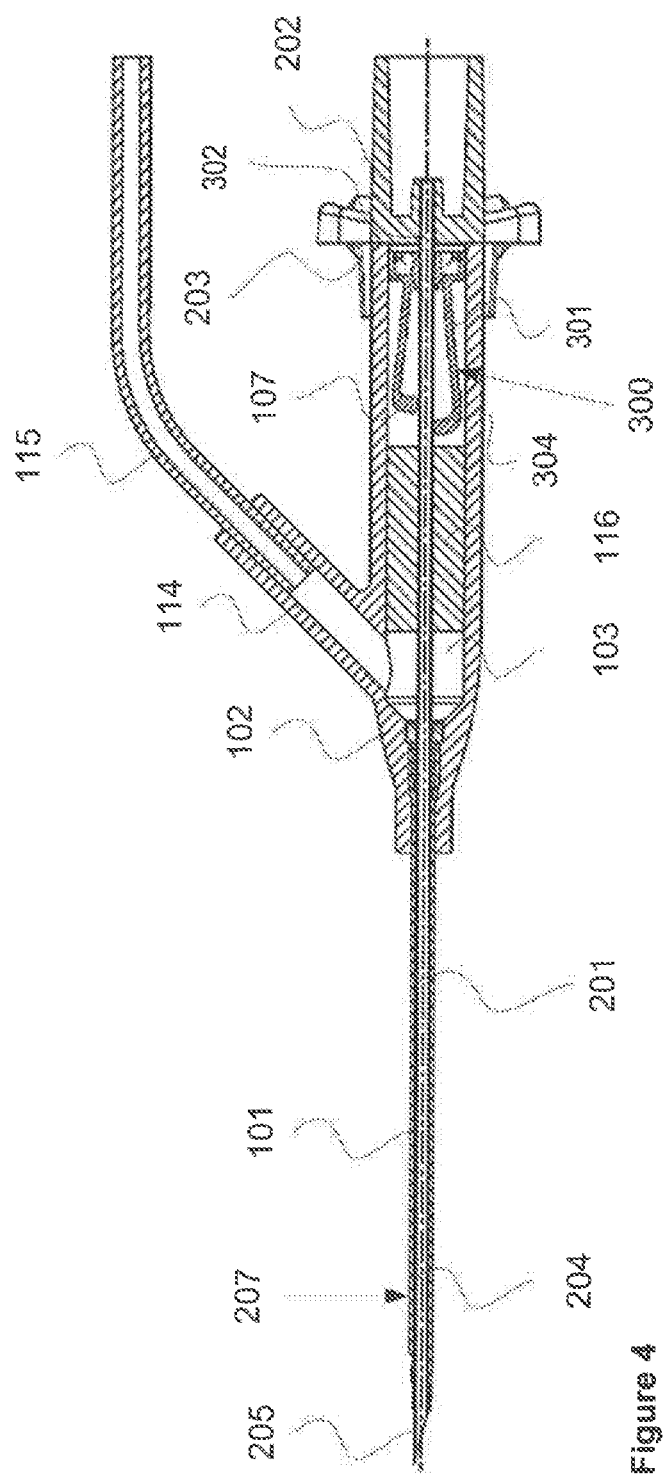
FIG. 4 is a cross-sectional view of a closed IV catheter system, with a catheter hub, a needle hub, and a needle shield, in assembled state, in accordance with an embodiment of the present invention.
Figure 5A:
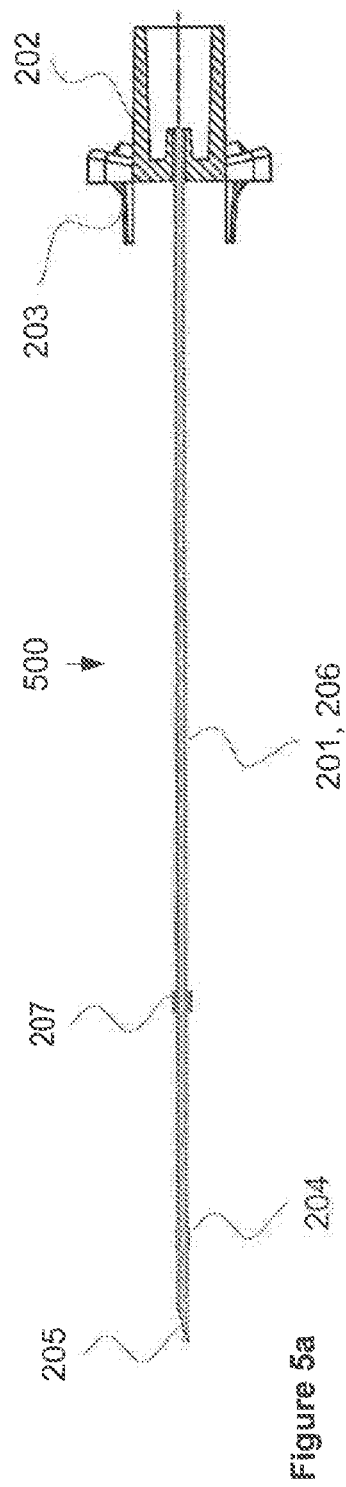
FIG. 5A is a side view of a needle system of the present disclosure.
Figure 5B:
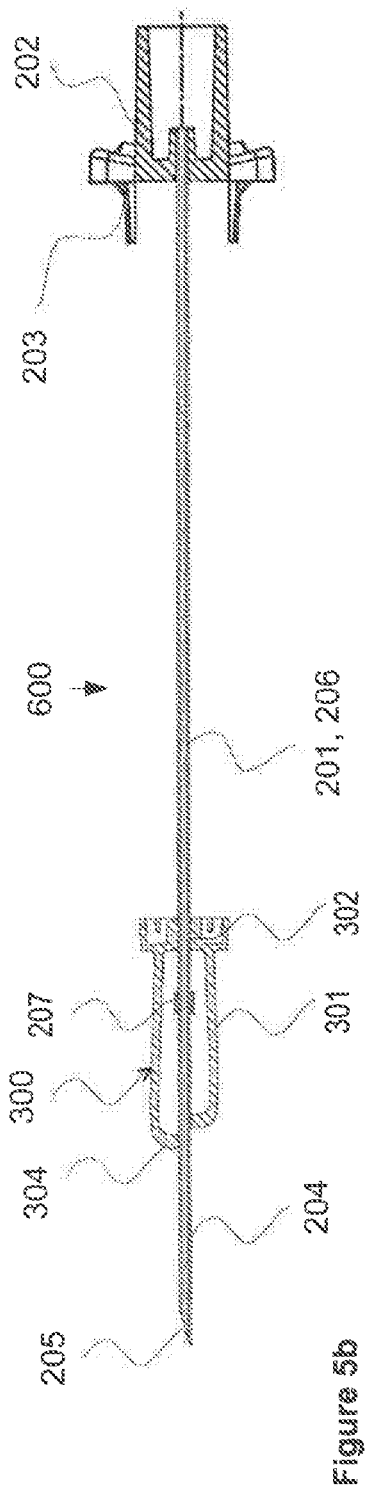
FIG. 5B is a side view of a shielded needle system and a needle shield of the present disclosure.

In one embodiment in accordance with FIG. 4, a tube connector 114 is provided on catheter hub body 102. The tube connector 114 extends laterally from the catheter hub body 112. The tube connector 114 has a lumen in fluid communication with the distal catheter hub cavity 103, such that a tube 115 may be connected to the tube connector 114 to allow for infusion from the tube 115 into the tube connector 114, further into distal catheter hub cavity 103 to catheter 101, and finally into the blood stream of the patient. The tube connector 114 may for example be tubular. A suitable material for the tube 115 is polyvinyl chloride or ethylene vinyl acetate. The catheter distal catheter hub cavity 103 ends proximally in a septum 116. This septum 116 has a central through channel, which may be penetrated by a needle 201 of a needle hub 200, in accordance with FIG. 2. When the needle 201 has been withdrawn from the catheter hub 100, the septum 116 will close said through channel, such that the distal catheter hub cavity 103 is marked off from the surroundings in the proximal direction. For this reason, the septum 116 is preferably of a suitable rubber material or silicone. On the proximal side of the septum 116 a proximal catheter hub cavity 107 is located. The proximal catheter hub cavity 107 is formed by the tubular wall of the catheter hub body 102 and a distal end wall in form of the proximal end wall of the septum 116. This proximal catheter hub cavity 107, extending distally into the catheter hub body 102, is adapted in size and shape to house the needle shield 300.

According to one embodiment, the needle shield 300 may be made of a plastic material. Preferably, the plastic material has a suitable combination, for its intended purpose, of tenacity, rigidity, fatigue resistance, elasticity, and creep deformation resistance. A suitable plastic material has a high creep deformation resistance, i.e. it has a low tendency to slowly move or deform permanently under the influence of an applied external pressure. Hence, a catheter system of the present invention, comprising needle shield 300, may be stored in the assembled ready mode for a prolonged time without extensive creep deformation of the arms 304 or the tongues 303. Advantages of a plastic needle shield 300 include the highly reduced tendency, in comparison to metal, of release of e.g. microscopic plastic chips by the scraping of the plastic catheter hub 100, when the needle shield 300, is ejected from the former upon withdrawal of the needle 201. Accordingly, the tendency for formation of scrape marks, which may result in leakage through the affected connector, is greatly reduced. In addition, a plastic needle tip 205 shielding device may be easily color coded or transparent, depending on its particular application.

The needle shield 300 is a monolithic or homogenous injection molded needle shielding 300, made of a molded plastic material. Due to the specific configuration of the different parts of the needle shield 300 according to the embodiments of the present invention, the needle shield 300 may be molded, such as injection molded, into one homogenous, i.e. monolithic, piece and/or one integral unit, without interfaces in between the different parts thereof. Advantages of a monolithic needle shield 300 include a lower production cost in comparison to other devices made of more than one part that has to be assembled. The needle shield 300 may in this respect be made of a thermoplastic polymer. The thermoplastic polymer could be crystalline, amorphous, or comprising crystalline and amorphous alternating regions. A creep resistance of the thermoplastic polymer of choice may preferably be at least 1200 MPa (ISO 527, ASTM D638). Suitable plastics for the needle shield 300 may be selected from the group comprising of polyoxymethylene (POM), polybutylen terephthalate (PBTP), polymethyl methacrylate (PMMA), acrylonitrile butadiene styrene (ABS), styrene acrylonitrile (SAN), acrylonitrile styrene acrylate (ASA), polystyrene (PS), styrene butadiene (SB), liquid crystal polymer (LCP), polyarnide (PA), polysulfone (PSU), polyetherimide (PEI), polycarbonate (PC), polyphenylene oxide (PPO), and/or PPO/SB, and co- and terpolymers thereof. These polymers have specifically the advantages of providing enhanced storing capacity, even in strained state, and excellent cooperation abilities with regard to the catheter hub, due to the excellent structure memory of these polymers.

Contacting smooth shapes of two bodies, such as a needle shield 300 mounted in a catheter hub 100, may result in a significant attraction between these bodies, especially if the contact area is large and they are pressed together. The underlying basis for this type of attraction include intermolecular attraction between the molecules of the two bodies, in which molecular van der Waals interactions and surface tension of the two bodies are important factors. Covalent bond formation between closely interacting surfaces may also contribute to the attraction. Such covalent bond formation, and other types of attraction between two surfaces, may also result upon radiation treatment, such as radiation treatment of e.g. catheter instrument to sterilize these. This type of attraction may become noticeable when the needle shield 300 is about to be released from the catheter hub 100. The force needed to release the needle shield 300 from the catheter hub 100 then becomes significantly higher than expected. This effect, which may be referred to as "the attraction effect", may even adventure the intended function of the needle tip 205 shielding device if relying on e.g. an automatic release of a part of the device, such as a spring biased arm or the like, from a part of the catheter hub. The needle shield 300 is kept in contact with the catheter hub 100 in the assembled state via at least one interface surface between the needle shield 300 and the catheter hub 100. Thus, in one embodiment the surface of the needle shield 300 being in contact with the inner lumen of the catheter hub is of a different polymeric material than the polymeric material of the catheter hub. Here, the high friction surface part 207 of the needle bulge 204 provides extra safety, since it makes it possible to exert additional pulling force on the needle shield in ease of such attraction.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "second" etc do not preclude a plurality. Reference signs in the claims are provided merely as a clarifying example and shall not be construed as limiting the scope of the claims in any way.

What is claimed is:

1. An IV catheter system comprising:
a catheter hub including a tubular catheter having a lumen being attached to a catheter hub body at its proximal end, the catheter hub body including a catheter hub cavity in fluid communication with the lumen of the tubular catheter;

a needle hub including a needle extending distally from a needle hub body, said needle having a needle bulge and a high friction surface part at its distal end zone, the needle bulge including opposing flattened sides that are circumferentially interposed by corresponding outwardly extending protrusions, and the high friction surface part covers the needle bulge and extends proximally and distally of the needle bulge along only a portion of a shaft of the needle;

a needle shield comprising at least one resilient arm extending distally from a base plate, said base plate having a through hole for receiving the needle therethrough;

wherein the needle hub is arranged in the catheter hub cavity in a retained manner through cooperation between the needle shield and an inner wall of the catheter hub in said catheter hub cavity, and onto the needle, such that the at least one arm rests upon and is spring loaded by the needle, and the needle is slidingly arranged within the through hole of the base plate, in an assembled state;

wherein the high friction surface part has a surface roughness in a range 0.75 to 10 $R_a$, and wherein an outer diameter of the needle bulge is larger than an inner diameter of the through hole of the base plate when the needle hub is withdrawn from the catheter hub to release the needle shield from the catheter hub and that the at least one arm will cover a trip of the needle in a released state.

2. The IV catheter system of claim 1, wherein a length of the high friction surface part is in a range of 0.2 to 20 mm.

3. The IV catheter system of claim 1, further comprising a connector, said connector extending laterally from the catheter hub body, located distally of a proximal portion of the catheter hub cavity.

4. The IV catheter system of claim 3, wherein the IV catheter system is an open IV catheter system, wherein the connector is an open connector in direct contact with a valve such that the connector, the proximal catheter hub cavity, and the distal catheter hub cavity are in fluid communication when the needle has been withdrawn from said valve.

5. The IV catheter system of claim 3, wherein the IV catheter system is a closed IV catheter system, wherein the connector is a tube connector in direct fluid connection with the distal hub cavity, wherein the tube connector may be connected to a tube; and a valve that is a septum, proximal of the distal catheter hub cavity and distal of the proximal catheter hub cavity, wherein a septum through-hole will close when the needle is withdrawn from the septum.

6. The IV catheter system of claim 1, further comprising a valve, said valve having a through hole for receiving the needle there through, wherein the valve is located between a distal catheter hub cavity and a proximal catheter hub cavity.

7. The IV catheter system of claim 1, wherein the high friction surface part is a section of a metal alloy of a needle shaft of the needle, wherein the high friction surface part is made rough through processes, and includes at least one of sandblasting, etching (chemical process), erosion, electron beam surface treatment, plasma treatment, electrical discharge machining, coating, and laser texturing.

8. The IV catheter system of claim 1, wherein the catheter hub body includes a polycarbonate or a copolymer of polycarbonate and polyester.

9. The IV catheter system of claim 1, further comprising a valve made of silicone or rubber.

10. The IV catheter system of claim 1, wherein a proximal end of the catheter hub body cooperates with a distal end of the needle hub body in the assembled state.

11. The IV catheter system of claim 1, wherein a distal connective flange of the needle hub body cooperates with an outer proximal surface of the catheter hub body in a retaining manner.

12. The IV catheter system of claim 1, wherein the needle shield cooperates with an inner wall of the catheter hub body in a proximal portion of the catheter hub cavity through a periphery of the base plate.

13. The IV catheter system of claim 1, wherein a periphery of the base plate is provided with at least one resilient tongue, which in turn cooperates with the catheter hub body.

14. The IV catheter system of claim 1, further comprising tongues evenly distributed along a periphery of the base plate.

15. The IV catheter system of claim 1, wherein the needle shield is a monolithic plastic body, wherein a plastic material of the needle shield is selected from the group consisting of POM, PBTP, PMMA, ABS, SAN, ASA, PS, SB, LCP, PA, PSU, PEI, PC, PPO, or PPO/SB.

16. The IV catheter system of claim 1, wherein the needle is made of metal, and wherein the high friction surface part covers an entire surface of the needle bulge.

17. A needle hub, said needle hub comprising: a needle extending distally from a needle hub body, said needle having a needle bulge and a high friction surface part at its distal end zone, the needle bulge including opposing flattened sides that are circumferentially interposed by outwardly extending protrusions, and the high friction surface part covers the needle bulge and extends proximally and distally of the needle bulge along a shaft of the needle, a length of the high friction surface part on the needle is in the range of 0.2 to 20 mm and does not cover an entire length of the needle, and a surface roughness of the high friction surface part is in a range of 0.25 to 10 $R_a$.

18. The needle hub of claim 17, wherein the needle bulge has a radius that is larger than a radius of the needle.

19. A shielded needle system, comprising:

a needle hub including a needle extending distally from a needle hub body, said needle having a needle bulge and a high friction surface part at its distal end zone, the needle bulge including opposing flattened sides that are circumferentially interposed by outwardly extending protrusions, and the high friction surface part covers the needle bulge and extends proximally and distally of the needle bulge along only a portion of a shaft of the needle, and has a surface roughness in a range of 0.5 to 5 $R_a$; and a needle shield;

said needle shield including at least one resilient arm extending distally from a base plate, said base plate having a through hole for receiving the needle therethrough; and wherein the needle shield is located between the needle bulge and a distal side of the needle hub body.

* * * * *